United States Patent
Marshall (10) Patent No.: US 9,731,119 B2
(45) Date of Patent: Aug. 15, 2017

(54) SYSTEM AND METHOD FOR IMPLANTABLE MEDICAL DEVICE LEAD SHIELDING

(71) Applicant: MEDTRONIC, INC., Minneapolis, MN (US)

(72) Inventor: Mark T. Marshall, Forest Lake, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 23 days.

(21) Appl. No.: 14/715,271

(22) Filed: May 18, 2015

(65) Prior Publication Data

US 2015/0246222 A1    Sep. 3, 2015

Related U.S. Application Data

(62) Division of application No. 12/112,889, filed on Apr. 30, 2008, now Pat. No. 9,037,263.
(Continued)

(51) Int. Cl.
*A61N 1/00* (2006.01)
*A61N 1/05* (2006.01)
(Continued)

(52) U.S. Cl.
CPC ............ *A61N 1/0563* (2013.01); *A61N 1/048* (2013.01); *A61N 1/0472* (2013.01); *A61N 1/08* (2013.01); *A61N 2001/086* (2013.01)

(58) Field of Classification Search
None
See application file for complete search history.

(56) References Cited

U.S. PATENT DOCUMENTS 2,433,480 A    12/1947  Rendich
2,487,038 A    11/1949  Jasper
(Continued)

FOREIGN PATENT DOCUMENTS

EP    0617978    10/1994
EP    0624383    11/1994
(Continued)

OTHER PUBLICATIONS

PCT/US2004/042081: Search Report and Written Opinion.
(Continued)

*Primary Examiner* — Edward Moran
*Assistant Examiner* — Elizabeth K So
(74) *Attorney, Agent, or Firm* — Withers & Keys, LLC (57) ABSTRACT

An implantable medical device (IMD) can include a cardiac pacemaker or an implantable cardioverter-defibrillator (ICD). Various portions of the IMD, such as a device body, a lead body, or a lead tip, can be provided to reduce or dissipate a current and heat induced by various external environmental factors. According to various embodiments, features can be incorporated into the lead body, the lead tip, or the IMD body to reduce the creation of an induced current, or dissipate the induced current and heat created due to an induced current in the lead. For example, an IMD can include at least one outer conductive member and a first electrode. The first electrode can be in electrical communication with the at least one outer conductive member. The first electrode can dissipate a current induced in the at least one outer conductive member via a first portion of the anatomical structure.

8 Claims, 6 Drawing Sheets

Related U.S. Application Data (60) Provisional application No. 61/035,956, filed on Mar. 12, 2008.

(51) Int. Cl.
*A61N 1/04* (2006.01)
*A61N 1/08* (2006.01)

(56) References Cited

U.S. PATENT DOCUMENTS

| | | |
|---|---|---|
| 3,788,329 A | 1/1974 | Friedman |
| 3,842,485 A | 10/1974 | Bemert |
| 3,915,174 A | 10/1975 | Preston |
| 4,033,355 A | 7/1977 | Amundson |
| 4,038,990 A | 8/1977 | Thompson |
| 4,214,804 A | 7/1980 | Little |
| 4,220,813 A | 9/1980 | Kyle |
| 4,280,507 A | 7/1981 | Rosenberg |
| 4,320,763 A | 3/1982 | Money |
| 4,350,169 A | 9/1982 | Dutcher |
| 4,383,225 A | 5/1983 | Mayer |
| 4,403,824 A | 9/1983 | Scott |
| 4,441,498 A | 4/1984 | Nordling |
| 4,628,942 A | 12/1986 | Sweeney et al. |
| 4,683,895 A | 8/1987 | Pohndorf |
| 4,711,027 A | 12/1987 | Harris |
| 4,726,379 A | 2/1988 | Altman et al. |
| 4,852,585 A | 8/1989 | Heath |
| 4,906,241 A | 3/1990 | Noddin |
| 4,920,980 A | 5/1990 | Jackowski |
| 4,922,607 A | 5/1990 | Doan et al. |
| 4,934,380 A | 6/1990 | de Toledo |
| 4,947,866 A | 8/1990 | Lessar et al. |
| 4,951,672 A | 8/1990 | Buchwald et al. |
| 4,991,583 A | 2/1991 | Silvian |
| 5,003,992 A | 4/1991 | Holleman |
| 5,005,587 A | 4/1991 | Scott |
| 5,012,045 A | 4/1991 | Sato |
| 5,018,523 A | 5/1991 | Bach, Jr. et al. |
| 5,020,544 A | 6/1991 | Dahl et al. |
| 5,020,545 A | 6/1991 | Soukup |
| 5,036,862 A | 8/1991 | Pohndorf |
| 5,040,544 A | 8/1991 | Lessar et al. |
| 5,063,932 A | 11/1991 | Dahl et al. |
| 5,197,468 A | 3/1993 | Proctor et al. |
| 5,213,111 A | 5/1993 | Cook et al. |
| 5,217,010 A | 6/1993 | Tsitlik et al. |
| 5,231,078 A | 7/1993 | Riebman et al. |
| 5,243,996 A | 9/1993 | Hall |
| 5,246,438 A | 9/1993 | Langberg |
| 5,260,128 A | 11/1993 | Ishii et al. |
| 5,265,608 A | 11/1993 | Lee et al. |
| 5,265,623 A | 11/1993 | Kroll et al. |
| 5,271,417 A | 12/1993 | Swanson et al. |
| 5,308,664 A | 5/1994 | House et al. |
| 5,314,459 A | 5/1994 | Swanson et al. |
| 5,323,776 A | 6/1994 | Blakely et al. |
| 5,335,657 A | 8/1994 | Terry, Jr. et al. |
| 5,349,133 A | 9/1994 | Rogers |
| 5,360,441 A | 11/1994 | Otten |
| 5,366,496 A | 11/1994 | Dahl et al. |
| 5,370,644 A | 12/1994 | Langberg |
| 5,374,286 A | 12/1994 | Morris |
| 5,374,778 A | 12/1994 | Hashimoto et al. |
| 5,417,719 A | 5/1995 | Hull et al. |
| 5,456,705 A | 10/1995 | Morris |
| 5,458,629 A | 10/1995 | Baudino et al. |
| 5,458,631 A | 10/1995 | Xavier |
| 5,466,252 A | 11/1995 | Soukup et al. |
| 5,473,812 A | 12/1995 | Morris et al. |
| 5,476,496 A | 12/1995 | Strandberg et al. |
| 5,485,667 A | 1/1996 | Kleshinski |
| 5,500,013 A | 3/1996 | Buscemi et al. |
| 5,504,274 A | 4/1996 | McCabe et al. |
| 5,514,172 A | 5/1996 | Mueller |
| 5,515,848 A | 5/1996 | Corbett, III et al. |
| 5,523,534 A | 6/1996 | Meister et al. |
| 5,523,578 A | 6/1996 | Herskovic |
| 5,527,348 A | 6/1996 | Winkler |
| 5,534,018 A | 7/1996 | Wahlstrand |
| 5,552,565 A | 9/1996 | Cartier et al. |
| 5,571,157 A | 11/1996 | McConnell |
| 5,572,594 A | 11/1996 | DeVoe et al. |
| 5,591,218 A | 1/1997 | Jacobson |
| 5,594,304 A | 1/1997 | Graber |
| 5,606,981 A | 3/1997 | Tartacower et al. |
| 5,609,622 A | 3/1997 | Soukup et al. |
| 5,628,780 A | 5/1997 | Helland et al. |
| 5,629,622 A | 5/1997 | Scampini |
| 5,643,254 A | 7/1997 | Scheldrup et al. |
| 5,649,965 A | 7/1997 | Pons et al. |
| 5,662,697 A | 9/1997 | Li et al. |
| 5,676,659 A | 10/1997 | McGurk |
| 5,676,694 A | 10/1997 | Boser et al. |
| 5,683,435 A | 11/1997 | Truex et al. |
| 5,683,444 A | 11/1997 | Huntley et al. |
| 5,697,909 A | 12/1997 | Eggers et al. |
| 5,697,958 A | 12/1997 | Paul et al. |
| 5,702,437 A | 12/1997 | Baudino |
| 5,706,826 A | 1/1998 | Schwager |
| 5,722,998 A | 3/1998 | Prutchi et al. |
| 5,727,552 A | 3/1998 | Ryan |
| 5,751,539 A | 5/1998 | Stevenson et al. |
| 5,766,232 A | 6/1998 | Grevious et al. |
| 5,782,241 A | 7/1998 | Felblinger et al. |
| 5,795,341 A | 8/1998 | Samson |
| 5,807,258 A | 9/1998 | Cimochowski et al. |
| 5,814,076 A | 9/1998 | Brownlee |
| 5,827,997 A | 10/1998 | Chung et al. |
| 5,830,136 A | 11/1998 | Delonzor et al. |
| 5,842,966 A | 12/1998 | Markoll |
| 5,842,986 A | 12/1998 | Avrin et al. |
| 5,851,226 A | 12/1998 | Skubitz et al. |
| 5,897,584 A | 4/1999 | Herman |
| 5,905,627 A | 5/1999 | Brendel et al. |
| 5,927,345 A | 7/1999 | Samson |
| 5,931,861 A | 8/1999 | Werner et al. |
| 5,954,760 A | 9/1999 | Jarl |
| 5,964,705 A | 10/1999 | Truwit et al. |
| 5,968,087 A | 10/1999 | Hess |
| 5,970,429 A | 10/1999 | Martin |
| 6,004,269 A | 12/1999 | Crowley |
| 6,016,447 A | 1/2000 | Juran et al. |
| 6,024,703 A | 2/2000 | Zanelli et al. |
| 6,032,063 A | 2/2000 | Hoar et al. |
| 6,033,408 A | 3/2000 | Gage et al. |
| 6,055,457 A | 4/2000 | Bonner |
| 6,101,417 A | 8/2000 | Vogel et al. |
| 6,103,037 A | 8/2000 | Wilson |
| 6,108,582 A | 8/2000 | Fischer, Sr. |
| 6,132,390 A | 10/2000 | Cookston et al. |
| 6,141,593 A | 10/2000 | Patag |
| 6,143,013 A | 11/2000 | Samson et al. |
| 6,152,746 A | 11/2000 | Brown |
| 6,156,029 A | 12/2000 | Mueller |
| 6,195,267 B1 | 2/2001 | MacDonald et al. |
| 6,198,807 B1 | 3/2001 | DeSena |
| 6,198,972 B1 | 3/2001 | Hartlaub et al. |
| 6,209,764 B1 | 4/2001 | Hartlaub et al. |
| 6,240,322 B1 | 5/2001 | Peterfeso |
| 6,258,071 B1 | 7/2001 | Brookes |
| 6,265,466 B1 | 7/2001 | Glatkowski |
| 6,269,148 B1 | 7/2001 | Jessop et al. |
| 6,284,971 B1 | 9/2001 | Atalar et al. |
| 6,302,740 B1 | 10/2001 | Holmstrom |
| 6,348,070 B1 | 2/2002 | Teissl et al. |
| 6,424,234 B1 | 7/2002 | Stevenson |
| 6,471,699 B1 | 10/2002 | Fleischman et al. |
| 6,488,704 B1 | 12/2002 | Connelly et al. |
| 6,494,916 B1 | 12/2002 | Babalola et al. |
| 6,501,991 B1 | 12/2002 | Honeck et al. |
| 6,503,648 B1 | 1/2003 | Wang |
| 6,506,972 B1 | 1/2003 | Wang |
| 6,529,774 B1 | 3/2003 | Greene |

(56) References Cited

U.S. PATENT DOCUMENTS

| | | |
|---|---|---|
| 6,538,191 B1 | 3/2003 | MacDonald |
| 6,583,361 B2 | 6/2003 | Clouet |
| 6,606,521 B2 | 8/2003 | Paspa et al. |
| 6,640,137 B2 | 10/2003 | MacDonald |
| 6,648,690 B2 | 11/2003 | Saito et al. |
| 6,660,116 B2 | 12/2003 | Wolf et al. |
| 6,671,544 B2 | 12/2003 | Baudino |
| 6,671,554 B2 | 12/2003 | Gibson et al. |
| 6,673,999 B1 | 1/2004 | Wang et al. |
| 6,675,033 B1 | 1/2004 | Lardo et al. |
| 6,689,835 B2 | 2/2004 | Amarasekera et al. |
| 6,695,761 B2 | 2/2004 | Oschman et al. |
| 6,708,051 B1 | 3/2004 | Durousseau |
| 6,711,440 B2 | 3/2004 | Deal et al. |
| 6,712,844 B2 | 3/2004 | Pacetti et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,735,471 B2 | 5/2004 | Hill et al. |
| 6,741,892 B1 | 5/2004 | Meadows et al. |
| 6,743,055 B1 | 6/2004 | Flynn |
| 6,750,055 B1 | 6/2004 | Connelly et al. |
| 6,757,566 B2 | 6/2004 | Weiner et al. |
| 6,760,628 B2 | 7/2004 | Weiner et al. |
| 6,763,268 B2 | 7/2004 | MacDonald et al. |
| 6,765,144 B1 | 7/2004 | Wang et al. |
| 6,768,053 B1 | 7/2004 | Wang et al. |
| 6,778,856 B2 | 8/2004 | Connelly et al. |
| 6,792,316 B2 | 9/2004 | Sass |
| 6,793,642 B2 | 9/2004 | Connelly et al. |
| 6,795,730 B2 | 9/2004 | Connelly et al. |
| 6,795,736 B2 | 9/2004 | Connelly et al. |
| 6,799,067 B2 | 9/2004 | Pacetti |
| 6,799,069 B2 | 9/2004 | Weiner et al. |
| 6,815,609 B1 | 11/2004 | Wang et al. |
| 6,819,954 B2 | 11/2004 | Connelly |
| 6,819,958 B2 | 11/2004 | Weiner et al. |
| 6,844,492 B1 | 1/2005 | Wang et al. |
| 6,845,259 B2 | 1/2005 | Pacetti et al. |
| 6,845,267 B2 | 1/2005 | Harrison et al. |
| 6,846,985 B2 | 1/2005 | Wang et al. |
| 6,850,805 B2 | 2/2005 | Connelly et al. |
| 6,852,091 B2 | 2/2005 | Edwards et al. |
| 6,863,653 B1 | 3/2005 | Zanelli et al. |
| 6,864,418 B2 | 3/2005 | Wang et al. |
| 6,869,683 B2 | 3/2005 | Sakurai et al. |
| 6,871,091 B2 | 3/2005 | Wilkinson et al. |
| 6,872,882 B2 | 3/2005 | Fritz |
| 6,875,180 B2 | 4/2005 | Weiner et al. |
| 6,879,861 B2 | 4/2005 | Benz et al. |
| 6,882,519 B2 | 4/2005 | Uzawa et al. |
| 6,895,280 B2 | 5/2005 | Meadows et al. |
| 6,901,287 B2 | 5/2005 | Davis et al. |
| 6,901,290 B2 | 5/2005 | Foster et al. |
| 6,906,256 B1 | 6/2005 | Wang |
| 6,920,361 B2 | 7/2005 | Williams |
| 6,922,590 B1 | 7/2005 | Whitehurst |
| 6,925,328 B2 | 8/2005 | Foster et al. |
| 6,930,242 B1 | 8/2005 | Helfer |
| 6,937,906 B2 | 8/2005 | Terry et al. |
| 6,944,489 B2 | 9/2005 | Zeijlemaker et al. |
| 6,949,929 B2 | 9/2005 | Gray et al. |
| 6,954,674 B2 | 10/2005 | Connelly |
| 6,968,235 B2 | 11/2005 | Belden et al. |
| 6,968,236 B2 | 11/2005 | Hagele |
| 6,971,391 B1 | 12/2005 | Wang et al. |
| 6,980,865 B1 | 12/2005 | Wang et al. |
| 6,982,378 B2 | 1/2006 | Dickson |
| 6,985,775 B2 | 1/2006 | Reinke et al. |
| 6,993,387 B2 | 1/2006 | Connelly et al. |
| 6,999,818 B2 | 2/2006 | Stevenson et al. |
| 6,999,821 B2 | 2/2006 | Jenney et al. |
| 7,001,369 B2 | 2/2006 | Griffin et al. |
| 7,013,174 B2 | 3/2006 | Connelly et al. |
| 7,013,180 B2 | 3/2006 | Villaseca et al. |
| 7,015,392 B1 | 3/2006 | Dickenson |
| 7,015,393 B2 | 3/2006 | Weiner |
| 7,047,084 B2 | 5/2006 | Erickson |
| 7,050,855 B2 | 5/2006 | Zeijlemaker et al. |
| 7,058,192 B2 | 6/2006 | Muller et al. |
| 7,076,283 B2 | 7/2006 | Cho et al. |
| 7,076,302 B2 | 7/2006 | Scheiner |
| 7,082,328 B2 | 7/2006 | Funke |
| 7,082,337 B2 | 7/2006 | Sommer et al. |
| 7,103,413 B2 | 9/2006 | Swanson |
| 7,113,827 B2 | 9/2006 | Silvestri |
| 7,115,134 B2 | 10/2006 | Chambers |
| 7,118,693 B2 | 10/2006 | Glatkowski et al. |
| 7,123,013 B2 | 10/2006 | Gray |
| 7,125,409 B2 | 10/2006 | Truckai et al. |
| 7,162,302 B2 | 1/2007 | Wang et al. |
| 7,174,219 B2 | 2/2007 | Wahlstrand et al. |
| 7,187,980 B2 | 3/2007 | Osypka et al. |
| 7,233,825 B2 | 6/2007 | Jorgenson et al. |
| 7,257,449 B2 | 8/2007 | Bodner |
| 7,282,260 B2 | 10/2007 | LeGrande et al. |
| 7,286,871 B2 | 10/2007 | Cohen |
| 7,286,882 B2 | 10/2007 | Cole |
| 7,292,894 B2 | 11/2007 | Belden |
| 7,294,785 B2 | 11/2007 | Uutela et al. |
| 7,319,901 B2 | 1/2008 | Dublin |
| 7,363,090 B2 | 4/2008 | Halperin |
| 7,389,148 B1 | 6/2008 | Morgan |
| 7,540,865 B2 | 6/2009 | Griffin et al. |
| 7,548,788 B2 | 6/2009 | Chinn et al. |
| 7,591,831 B2 | 9/2009 | Parsonage et al. |
| 7,674,972 B2 | 3/2010 | Gladd et al. |
| 7,711,436 B2 | 5/2010 | Stone |
| 7,729,777 B2 | 6/2010 | Gray et al. |
| 7,738,942 B2 | 6/2010 | Weiner |
| 7,813,811 B2 | 10/2010 | Wingeier et al. |
| 7,819,826 B2 | 10/2010 | Diederich et al. |
| 7,822,484 B1 | 10/2010 | Zhao et al. |
| 7,828,833 B2 | 11/2010 | Haverkost |
| 7,844,343 B2 | 11/2010 | Wahlstrand |
| 7,844,344 B2 | 11/2010 | Wahlstrand |
| 7,853,332 B2 | 12/2010 | Olsen |
| 7,877,150 B2 | 1/2011 | Hoegh et al. |
| 7,904,178 B2 | 3/2011 | Williams |
| 7,917,213 B2 | 3/2011 | Bulkes |
| 7,933,652 B2 | 4/2011 | Phillips |
| 8,007,440 B2 | 8/2011 | Magnin et al. |
| 8,027,736 B2 | 9/2011 | Wahlstrand |
| 8,036,756 B2 | 10/2011 | Swoyer et al. |
| 8,048,060 B2 | 11/2011 | Griffin et al. |
| 8,055,351 B2 | 11/2011 | Atalar et al. |
| 8,106,657 B2 | 1/2012 | Sakellariou et al. |
| 8,170,691 B2 | 5/2012 | Eckerdal |
| 8,202,259 B2 | 6/2012 | Evans et al. |
| 8,246,643 B2 | 8/2012 | Nita |
| 8,275,464 B2 | 9/2012 | Li et al. |
| 8,280,526 B2 | 10/2012 | Wahlstrand |
| 8,483,842 B2 | 7/2013 | Alexander et al. |
| 8,620,455 B2 | 12/2013 | Alexander et al. |
| 8,676,340 B2 | 3/2014 | Wahlstrand |
| 8,744,598 B2 | 6/2014 | Alexander et al. |
| 8,788,061 B2 | 7/2014 | Mehdizadeth |
| 8,805,534 B2 | 8/2014 | Olsen |
| 8,903,504 B2 | 12/2014 | Hegland |
| 9,002,474 B2 | 4/2015 | Olsen |
| 9,037,263 B2 | 5/2015 | Marshall |
| 9,044,593 B2 | 6/2015 | Li |
| 2001/0044646 A1 | 11/2001 | Marshall et al. |
| 2002/0032468 A1 | 3/2002 | Hill |
| 2002/0038135 A1 | 3/2002 | Connelly et al. |
| 2002/0058978 A1 | 5/2002 | Sass |
| 2002/0082673 A1 | 6/2002 | Benz et al. |
| 2002/0106918 A1 | 8/2002 | Saito et al. |
| 2002/0111659 A1 | 8/2002 | Davis et al. |
| 2002/0111663 A1 | 8/2002 | Dahl et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |

(56) References Cited

U.S. PATENT DOCUMENTS

| | | |
|---|---|---|
| 2002/0116034 A1 | 8/2002 | Miller et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0143377 A1 | 10/2002 | Wessman et al. |
| 2002/0183438 A1 | 12/2002 | Amarasekera et al. |
| 2002/0183740 A1 | 12/2002 | Edwards et al. |
| 2002/0183822 A1 | 12/2002 | Bodner |
| 2002/0188345 A1 | 12/2002 | Pacetti |
| 2003/0009207 A1 | 1/2003 | Paspa et al. |
| 2003/0014080 A1 | 1/2003 | Baudino |
| 2003/0036776 A1 | 2/2003 | Foster et al. |
| 2003/0044623 A1 | 3/2003 | Sakurai et al. |
| 2003/0045920 A1 | 3/2003 | Belden et al. |
| 2003/0060732 A1 | 3/2003 | Jacobsen et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0093107 A1 | 5/2003 | Parsonage et al. |
| 2003/0109901 A1 | 6/2003 | Greatbatch |
| 2003/0117787 A1 | 6/2003 | Nakauchi |
| 2003/0120148 A1 | 6/2003 | Pacetti |
| 2003/0120197 A1 | 6/2003 | Kaneko et al. |
| 2003/0135114 A1 | 7/2003 | Pacetti et al. |
| 2003/0139794 A1 | 7/2003 | Jenney et al. |
| 2003/0139806 A1 | 7/2003 | Haverkost et al. |
| 2003/0140931 A1 | 7/2003 | Zeijlemaker |
| 2003/0144704 A1 | 7/2003 | Terry |
| 2003/0144705 A1 | 7/2003 | Funke |
| 2003/0144716 A1 | 7/2003 | Reinke et al. |
| 2003/0144717 A1 | 7/2003 | Hegele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0167052 A1 | 9/2003 | Lee et al. |
| 2003/0204217 A1 | 10/2003 | Greatbatch |
| 2003/0225331 A1 | 12/2003 | Diederich et al. |
| 2004/0020674 A1 | 2/2004 | McFadden et al. |
| 2004/0024442 A1 | 2/2004 | Sowinski et al. |
| 2004/0028859 A1 | 2/2004 | LeGrande et al. |
| 2004/0068307 A1 | 4/2004 | Goble |
| 2004/0071949 A1 | 4/2004 | Glatkowski et al. |
| 2004/0088012 A1 | 5/2004 | Kroll et al. |
| 2004/0106958 A1 | 6/2004 | Mathis et al. |
| 2004/0162600 A1 | 8/2004 | Williams |
| 2004/0167443 A1 | 8/2004 | Shireman et al. |
| 2004/0173368 A1 | 9/2004 | Dickson |
| 2004/0199069 A1 | 10/2004 | Connelly et al. |
| 2004/0220549 A1 | 11/2004 | Dittman et al. |
| 2004/0249428 A1 | 12/2004 | Wang et al. |
| 2004/0251042 A1 | 12/2004 | Weiner et al. |
| 2004/0263172 A1 | 12/2004 | Gray et al. |
| 2004/0263173 A1 | 12/2004 | Gray |
| 2004/0263174 A1 | 12/2004 | Gray et al. |
| 2004/0267328 A1 | 12/2004 | Duffin |
| 2005/0065587 A1 | 3/2005 | Gryzwa |
| 2005/0070972 A1 | 3/2005 | Wahlstrand |
| 2005/0080471 A1 | 4/2005 | Chitre et al. |
| 2005/0113876 A1 | 5/2005 | Weiner |
| 2005/0115624 A1 | 6/2005 | Walak |
| 2005/0137664 A1 | 6/2005 | Sommer et al. |
| 2005/0145307 A1 | 7/2005 | Shireman et al. |
| 2005/0159661 A1 | 7/2005 | Connelly et al. |
| 2005/0182471 A1 | 8/2005 | Wang |
| 2005/0222642 A1 | 10/2005 | Przybyszewski |
| 2005/0222647 A1 | 10/2005 | Wahlstrand |
| 2005/0222656 A1 | 10/2005 | Wahlstrand |
| 2005/0222657 A1 | 10/2005 | Wahlstrand |
| 2005/0222658 A1 | 10/2005 | Hoegh et al. |
| 2005/0222659 A1 | 10/2005 | Olsen |
| 2006/0030918 A1 | 2/2006 | Chinn et al. |
| 2006/0036306 A1 | 2/2006 | Heist et al. |
| 2006/0079926 A1 | 4/2006 | Desai et al. |
| 2006/0089680 A1 | 4/2006 | Bruchmann et al. |
| 2006/0095078 A1 | 5/2006 | Tronnes |
| 2006/0135962 A1 | 6/2006 | Kick et al. |
| 2006/0155270 A1 | 7/2006 | Hancock |
| 2006/0167522 A1 | 7/2006 | Malinowski |
| 2006/0167527 A1 | 7/2006 | Malinowski |
| 2006/0200218 A1 | 9/2006 | Wahlstrand |
| 2006/0224207 A1 | 10/2006 | Dublin |
| 2006/0247747 A1 | 11/2006 | Olsen |
| 2006/0247748 A1 | 11/2006 | Wahlstrand |
| 2007/0021811 A1 | 1/2007 | D'Aquanni et al. |
| 2007/0106332 A1 | 5/2007 | Denker |
| 2007/0123805 A1 | 5/2007 | Shireman et al. |
| 2007/0129779 A1 | 6/2007 | Ayre |
| 2007/0168008 A1 | 7/2007 | Olsen |
| 2007/0185556 A1 | 8/2007 | Williams |
| 2007/0208383 A1 | 9/2007 | Williams |
| 2007/0293924 A1 | 12/2007 | Belden et al. |
| 2008/0033497 A1 | 2/2008 | Bulkes |
| 2008/0039709 A1 | 2/2008 | Karmarkar |
| 2008/0058715 A1 | 3/2008 | Houser et al. |
| 2008/0154326 A1 | 6/2008 | Clyne |
| 2008/0183263 A1 | 7/2008 | Alexander |
| 2008/0195186 A1 | 8/2008 | Li |
| 2008/0195187 A1 | 8/2008 | Li |
| 2008/0215008 A1 | 9/2008 | Nance et al. |
| 2008/0242944 A1 | 10/2008 | Sharma |
| 2008/0243081 A1 | 10/2008 | Nance et al. |
| 2008/0243218 A1 | 10/2008 | Bottomley |
| 2008/0262582 A1 | 10/2008 | Alexander |
| 2008/0262584 A1 | 10/2008 | Bottomley |
| 2008/0269863 A1 | 10/2008 | Alexander |
| 2008/0287804 A1 | 11/2008 | Nita |
| 2009/0204192 A1 | 8/2009 | Carlton |
| 2009/0221970 A1 | 9/2009 | Spinoza |
| 2009/0228074 A1 | 9/2009 | Edgell et al. |
| 2009/0234402 A1 | 9/2009 | Marshall |
| 2009/0240235 A1 | 9/2009 | Murata |
| 2009/0259272 A1 | 10/2009 | Reddy |
| 2009/0270956 A1 | 10/2009 | Vase |
| 2009/0287189 A1 | 11/2009 | Suwito |
| 2010/0069743 A1 | 3/2010 | Sheetz et al. |
| 2010/0100164 A1 | 4/2010 | Johnson et al. |
| 2010/0137957 A1 | 6/2010 | Eckerdal |
| 2010/0145426 A1 | 6/2010 | Stone |
| 2010/0198327 A1 | 8/2010 | Helland |
| 2010/0256528 A1 | 10/2010 | Lippert et al. |
| 2010/0256604 A1 | 10/2010 | Lippert et al. |
| 2010/0268310 A1 | 10/2010 | Bonde et al. |
| 2010/0331938 A1 | 12/2010 | Sommer |
| 2011/0015713 A1 | 1/2011 | Min |
| 2011/0034983 A1 | 2/2011 | Min |
| 2011/0071599 A1 | 3/2011 | Olsen |
| 2011/0071604 A1 | 3/2011 | Wahlstrand |
| 2011/0071605 A1 | 3/2011 | Wahlstrand |
| 2011/0112615 A1 | 5/2011 | Hoegh et al. |
| 2011/0230943 A1 | 9/2011 | Johnson et al. |
| 2011/0251487 A1 | 10/2011 | Magnin et al. |
| 2011/0319905 A1 | 12/2011 | Palme et al. |
| 2012/0010689 A1 | 1/2012 | Wahlstrand |
| 2012/0035616 A1 | 2/2012 | Olsen et al. |
| 2012/0035694 A1 | 2/2012 | Olsen |
| 2012/0035695 A1 | 2/2012 | Olsen et al. |
| 2012/0035696 A1 | 2/2012 | Kern |
| 2012/0035697 A1 | 2/2012 | Stone |
| 2012/0035951 A1 | 2/2012 | Goetz |
| 2012/0041528 A1 | 2/2012 | Mehdizadeh et al. |
| 2012/0041529 A1 | 2/2012 | Olsen |

(56) References Cited

U.S. PATENT DOCUMENTS

| | | |
|---|---|---|
| 2012/0046722 A1 | 2/2012 | Olsen |
| 2012/0635696 | 2/2012 | Kern |
| 2012/0053664 A1 | 3/2012 | Hegland |
| 2012/0059467 A1 | 3/2012 | Drew |
| 2012/0130461 A1 | 5/2012 | Olsen |
| 2012/0330383 A1 | 12/2012 | Wahlstrand |
| 2013/0296991 A1 | 11/2013 | Alexander et al. |
| 2014/0107746 A1 | 4/2014 | Alexander et al. |
| 2014/0200643 A1 | 7/2014 | Wahlstrand |
| 2014/0288626 A1 | 9/2014 | Alexander et al. |
| 2014/0345132 A1 | 11/2014 | Mehdizadeh et al. |
| 2014/0350654 A1 | 11/2014 | Olsen et al. |
| 2015/0082618 A1 | 3/2015 | Hegland |
| 2015/0170792 A1 | 6/2015 | Alford |

FOREIGN PATENT DOCUMENTS

| | | |
|---|---|---|
| EP | 0713714 | 5/1996 |
| EP | 0760196 | 3/1997 |
| EP | 0920239 | 6/1999 |
| EP | 1273922 | 1/2003 |
| EP | 1424095 | 6/2004 |
| EP | 1466576 | 10/2004 |
| EP | 1625875 | 2/2006 |
| EP | 1632265 | 3/2006 |
| EP | 1935449 | 6/2008 |
| GB | 2429154 | 2/2007 |
| JP | 07/255863 | 10/1995 |
| JP | 11/086641 | 3/1999 |
| WO | WO95/32673 | 12/1995 |
| WO | WO96/16694 | 6/1996 |
| WO | WO96/28951 | 9/1996 |
| WO | WO97/41923 | 11/1997 |
| WO | WO98/48896 | 11/1998 |
| WO | WO99/10035 | 3/1999 |
| WO | WO99/19020 | 4/1999 |
| WO | WO99/60370 | 11/1999 |
| WO | WO00/27279 | 5/2000 |
| WO | WO01/80940 | 11/2001 |
| WO | WO02/00292 | 1/2002 |
| WO | WO02/083236 | 10/2002 |
| WO | WO03/037429 | 5/2003 |
| WO | WO03/061755 | 7/2003 |
| WO | WO03/063946 | 8/2003 |
| WO | WO03/063948 | 8/2003 |
| WO | WO03/063952 | 8/2003 |
| WO | WO03/063953 | 8/2003 |
| WO | WO03/063954 | 8/2003 |
| WO | WO03/063955 | 8/2003 |
| WO | WO03/063956 | 8/2003 |
| WO | WO03/063957 | 8/2003 |
| WO | WO03/075797 | 9/2003 |
| WO | WO03/092326 | 11/2003 |
| WO | WO03/095022 | 11/2003 |
| WO | WO2004/012809 | 2/2004 |
| WO | WO2004/052448 | 6/2004 |
| WO | WO2004/073040 | 8/2004 |
| WO | WO2005/030322 | 4/2005 |
| WO | WO2005/032654 | 4/2005 |
| WO | WO2005/102444 | 11/2005 |
| WO | WO2005/102445 | 11/2005 |
| WO | WO2005/102446 | 11/2005 |
| WO | WO2005/102447 | 11/2005 |
| WO | WO2006/031317 | 3/2006 |
| WO | WO2006/093685 | 9/2006 |
| WO | WO2006/093686 | 9/2006 |
| WO | WO2006/118640 | 11/2006 |
| WO | WO2006/118641 | 11/2006 |
| WO | WO2007/047966 | 4/2007 |
| WO | WO2007/124273 | 11/2007 |
| WO | WO2007/126657 | 11/2007 |
| WO | WO2007/149757 | 12/2007 |
| WO | WO2008/088568 | 7/2008 |
| WO | WO2008/100839 | 8/2008 |
| WO | WO2008/100840 | 8/2008 |
| WO | WO2008/111986 | 9/2008 |
| WO | WO2008/130409 | 10/2008 |
| WO | WO2008/134196 | 11/2008 |
| WO | WO2008/140376 | 11/2008 |
| WO | WO2009/011440 | 9/2009 |
| WO | WO2009/134901 | 11/2009 |
| WO | WO2010/062988 | 6/2010 |
| WO | WO2010/126871 | 11/2010 |
| WO | WO2010/126877 | 11/2010 |
| WO | WO2010/126884 | 11/2010 |
| WO | WO2010/126887 | 11/2010 |
| WO | WO2010/126935 | 11/2010 |
| WO | WO2010/126939 | 11/2010 |
| WO | WO2010/126943 | 11/2010 |
| WO | WO2010/126946 | 11/2010 |
| WO | WO2010/126949 | 11/2010 |
| WO | WO2010/126975 | 11/2010 |
| WO | WO2010/135440 | 11/2010 |
| WO | WO2011/019416 | 2/2011 |
| WO | WO2012/103419 | 8/2012 |
| WO | WO2013/158189 | 10/2013 |

OTHER PUBLICATIONS

PCT/US2005/000322: Search Report and Written Opinion.
PCT/US2008/053540: Search Report and Written Opinion.
PCT/US2008/053541: Search Report and Written Opinion.
PCT/US2008/059358: Search Report and Written Opinion.
PCT/US2009/036461: Search Report and Written Opinion.
PCT/US2010/032516: Search Report and Written Opinion.
PCT/US2010/032526: Search Report and Written Opinion.
PCT/US2010/032543: Search Report and Written Opinion.
PCT/US2010/032560: Search Report and Written Opinion.
PCT/US2010/032567: Search Report and Written Opinion.
PCT/US2010/032666: Search Report and Written Opinion.
PCT/US2010/032671: Search Report and Written Opinion.
PCT/US2010/032675: Search Report and Written Opinion.
PCT/US2010/032682: Search Report and Written Opinion.
PCT/US2010/032719: Search Report and Written Opinion.
PCT/US2013/023637: Search Report and Written Opinion.
Baker et al., "Evaluation of Specific Absorption Rates as a Dosimeter of MRI-Related Implant Heating", Journal of Magnetic Resonance Imaging 20:315-320 (2004).
Baker, K., et al., "Neurostimulation Systems: Assessment of Magnetic Field Interactions Associated with 1.5 and 3-Tesla MR Systems", J. Magn. Reson. Imaging, Jan. 2005, 21(1);72-7.
Chung, D.D.L., "Carbon Fiber Composites", 1994, chapter 1, p. 8, table 1.2, Elsevier, ISBN: 978-0-7506-9169-7.
Chung, D.D.L., Comparison of Submicron-Diameter Carbon Filaments and Conventional Carbon Fibers as Fillers in Composite Materials, Carbon 39 (2001) pp. 1119-1125, Elsevier Science Ltd.
Chung, D.D.L., Electromagnetic Interference Shielding Effectiveness of Carbon Materials, Carbon 29 (2001) pp. 279-285, Elsevier Science Ltd.
Engdahl, Tomi, "Ground Loop Basics." Web Jan. 4, 2009, ePanorama.net www.epanorama.net/documents/groundloop/basics.html 28052.00 U.S. Appl. No. 11/739,787.
Finelli, D., et al., "MRI Imaging-Related Heating of Deep Brain Stimulation Electrodes: in Vitro Study", AJNR Am. J. Neuroadiol 23:1, Nov./Dec. 2002.
Jou, W.S. "A Novel Structure of Woven Continuous-Carbon Fiber Composites with High Electromagnetic Shielding", Journal of Electronic Materials, vol. 33, No. 3, Mar. 1, 2004, pp. 162-170(9), Minerals, Metals and Materials Society, http://findarticles.com/p/articles/mi_qu3776/is_200403/ai_n9405_582/print.
Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.
Kolin, et al., "An Electromagnetic Intravascular Blood-Flow Sensor", Department of Biophysics, University of California School of Medicine (Los Angeles), Mar. 20, 1967, Proc. N.A.S., vol. 57, pp. 1331-1337.

(56) References Cited

OTHER PUBLICATIONS

Kolin, et al., "Miniaturization of the Electromagnetic Blood Flow Meter and Its Use for the Recording of Circulatory Responses of Conscious Animals to Sensory Stimuli", Department of Biophysics, University of California at Los Angeles, Aug. 1959, Proc. N.A.S. vol. 45(8), pp. 1312-1321.
Medtronic Activa Product Family and Procedure Solution Brochure, Medtronic, Inc, 2001.
Medtronic Neurostimulation Systems Brochure, Medtronic, Inc., 2002.
Quick et al., "Endourethral Mri", Magnetic Resonance in Medicine, 45:138-146, 2001.
Rezai, A., et al., "Neurostimulation System Used for Deep Brain Stimulation (DBS): MR Safety Issues and Implications of Failing to Follow Safety Recommendations" Investigative Radiology, May 2004, vol. 39, Issue 5, pp. 300-303.
Rezai, A., et al., "Neurostimulation Systems for Deep Brain Stimulation in Vitro Evaluation of Magnetic Resonance Imaging-Related Healing at 1.5 Tesla", Journal of Magnetic Reson. Imaging 2002; 15:241-50.

SYSTEM AND METHOD FOR IMPLANTABLE MEDICAL DEVICE LEAD SHIELDING

CROSS-REFERENCE

This application claims the benefit of U.S. Provisional Application No. 61/035,956, filed on Mar. 12, 2008. The disclosure of the above application is incorporated herein by reference.

FIELD

The present disclosure relates to implantable medical devices (IMDs), in particular to a system and method for shielding a cardiac lead system from radio frequency (RF) energy.

BACKGROUND

The statements in this section merely provide background information related to the present disclosure and may not constitute prior art.

The human anatomy includes many types of tissue that can either voluntarily or involuntarily, perform certain functions. However, after disease or injury, certain tissues may no longer operate within general anatomical norms. For example, after disease, injury, age, or combinations thereof, the heart muscle may begin to experience certain failures or deficiencies. Some of these failures or deficiencies can be corrected or treated with IMDs. These devices can include implantable pulse generator (IPG) devices, pacemakers, implantable cardioverter-defibrillator (ICD) devices, cardiac resynchronization therapy defibrillator devices, or combinations thereof.

One of the main portions of the IMD can include a lead that is directly connected to tissue to be affected by the IMD. The lead can include a tip portion that is directly connected to the anatomical tissue, such as a muscle bundle, and a lead body that connects to the device body or therapeutic driving device. It is generally known that the device body or case portion can be implanted in a selected portion of the anatomical structure, such as in a chest or abdominal wall, and the lead can be inserted through various venous portions so that the tip portion can be positioned at the selected position near or in the muscle group.

The IMD generally remains with the patient during the rest of the patient's natural life. To that end, the IMD can be exposed to various environmental factors. For example, the patient may undergo a magnetic resonance imaging (MRI) procedure or other high frequency imaging procedures. In this case, portions of the IMD may act as an antenna and have current and thermal energy induced therein due to the MRI procedure. Accordingly, reduction or dissipation of the induced current or thermal energy may be useful in certain circumstances.

SUMMARY

An implantable medical device (IMD) can include implantable pulse generator (IPG) devices, implantable cardioverter-defibrillators (ICD), cardiac resynchronization therapy defibrillator devices, neurostimulators or combinations thereof. The IMD can be positioned in a selected portion of the anatomical structure, such as a chest wall or abdominal wall, and a lead can be positioned through a vein or transvenously so that a lead tip can be implanted in a portion of the cardiac or heart muscle. Various portions of the IMD, such as a case or device body, the lead body, or the lead tip, can be formed or augmented to reduce or dissipate heat production due to various external environmental factors. For example, a magnetic and/or electric field from a magnetic resonance imager (MRI), diathermy (including shortwave, microwave, ultrasound, or the like) or other energy field producing devices can induce currents in the lead. According to various embodiments, features or portions can be incorporated into the lead body, the lead tip, or the device body to reduce the creation of an induced current, or dissipate or increase the area of dissipation of thermal energy created due to an induced current in the lead.

An implantable medical device operable to provide a therapy to an anatomical structure is provided. The device can include a lead having a proximal end, a distal end and at least one outer conductive member and a multilumen member that extends from the proximal end to the distal end. The device can also include a first electrode fixedly coupled between the proximal end and the distal end of the lead such that the first electrode can be positioned adjacent to a first portion of the anatomical structure, the first electrode in electrical communication with a first inner conductor disposed within the multilumen member to deliver a therapy to the first portion of the anatomical structure. The first electrode can be in electrical communication with the at least one outer conductive member and can have a first surface area. The device can also include a second electrode that can be coupled to the distal end of the lead. The second electrode in electrical communication with a second inner conductor disposed within the multilumen member to deliver a therapy to a second portion of the anatomical structure. The second electrode can have a second surface area. The first surface area can be greater than the second surface area. The first electrode can dissipate a current induced in the at least one outer conductive member via the first portion of the anatomical structure.

Provided is an implantable medical device operable to provide a therapy to an anatomical structure. The device can include a therapy device implanted in a portion of the anatomical structure and operable to generate the therapy for the anatomical structure. The device can also include a lead having a proximal end, a distal end and a lead body that includes a first outer conductive braid, a second outer conductive braid and a multilumen member. The first outer conductive braid and the second outer conductive braid can be disposed about the multilumen member. The device can include a first electrode fixedly coupled between the proximal end and the distal end of the lead such that the first electrode is positioned adjacent to a first portion of the anatomical structure. The first electrode can be in communication with the first outer conductive braid and the second outer conductive braid. The device can also include a first inner conductor that can pass through a portion of the multilumen member. The first inner conductor can be in electrical communication with the first electrode to deliver a therapy to the first portion of the anatomical structure. The device can include a tip electrode extending beyond the distal end of the lead and a tip inner conductor that can pass through a portion of the multilumen member. The tip inner conductor can be in electrical communication with the tip electrode to deliver a therapy to a second portion of the anatomical structure. The device can include a second electrode coupled adjacent to the tip electrode at the distal end of the lead such that the second electrode is positioned adjacent to a third portion of the anatomical structure. The device can further include a second inner conductor that can pass through a portion of the multilumen member. The second inner conductor can be in electrical communication with the second electrode to deliver a therapy to the third portion of the anatomical structure. The first outer conductive braid can be disposed between the proximal end of the lead and the first electrode, and the second outer conductive braid can be disposed between the first electrode and the second electrode. The first electrode can dissipate a current induced in the first outer conductive braid and second outer conductive braid, via the first portion of the anatomical structure.

Further provided is a method of forming a cardiac lead system for implantation into an anatomical structure. The method can include providing a lead having a multilumen member that can pass through the lead, a first electrode in electrical communication with a first inner conductor and fixedly coupled to the multilumen member, the first inner conductor passing through a portion of the multilumen member, and a second electrode in electrical communication with a second inner conductor and extending beyond an end of the multilumen member, the second inner conductor passing through a portion of the multilumen member. The method can also include providing the first electrode with a first surface area and the second electrode with a second surface area, with the first surface area being larger than the second surface area. The method can include covering a substantial portion of the lead with a shield, and electrically coupling the shield to the first electrode.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. As indicated above, the present teachings are directed towards providing a system and method for shielding a cardiac lead system from RF energy. It should be noted, however, that the present teachings could be applicable to any appropriate procedure in which it is desirable to shield a component from external electrical fields. Therefore, it will be understood that the following discussions are not intended to limit the scope of the appended claims.

Figure 1:
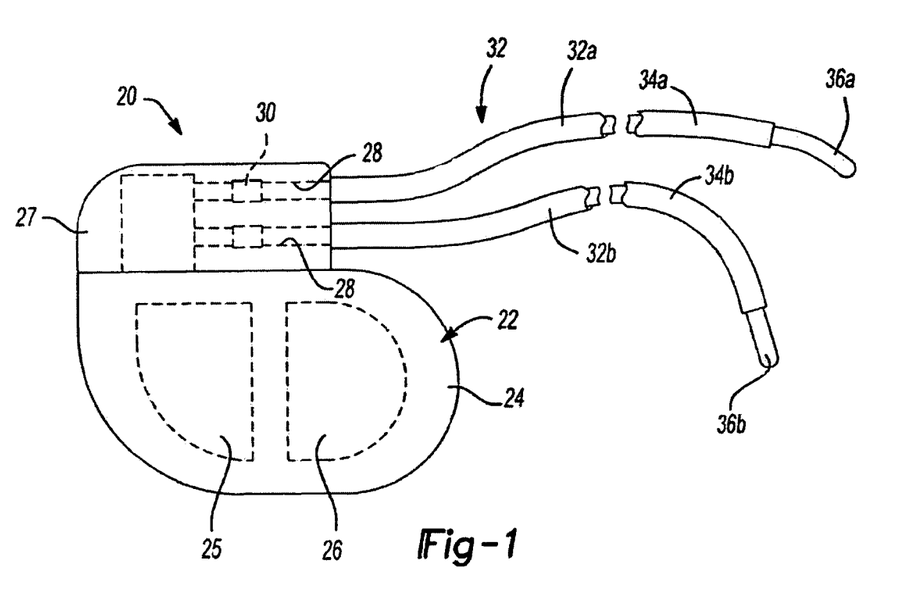
FIG. 1 is a view of an IMD including a lead connected to a device body.

With reference to FIG. 1, an implantable medical device (IMD) 20, which can include implantable pulse generator (IPG) devices, implantable cardioverter-defibrillator (ICD) devices, cardiac resynchronization therapy defibrillator devices, or combinations thereof, is exemplarily illustrated. The IMD 20 can include an implantable case or body assembly 22. The implantable case 22 can be formed of appropriate materials and include appropriate features, such as a hermetically sealed body wall 24. The body wall 24 can be made of a substantially inert material or of a conducting material.

Figure 2:
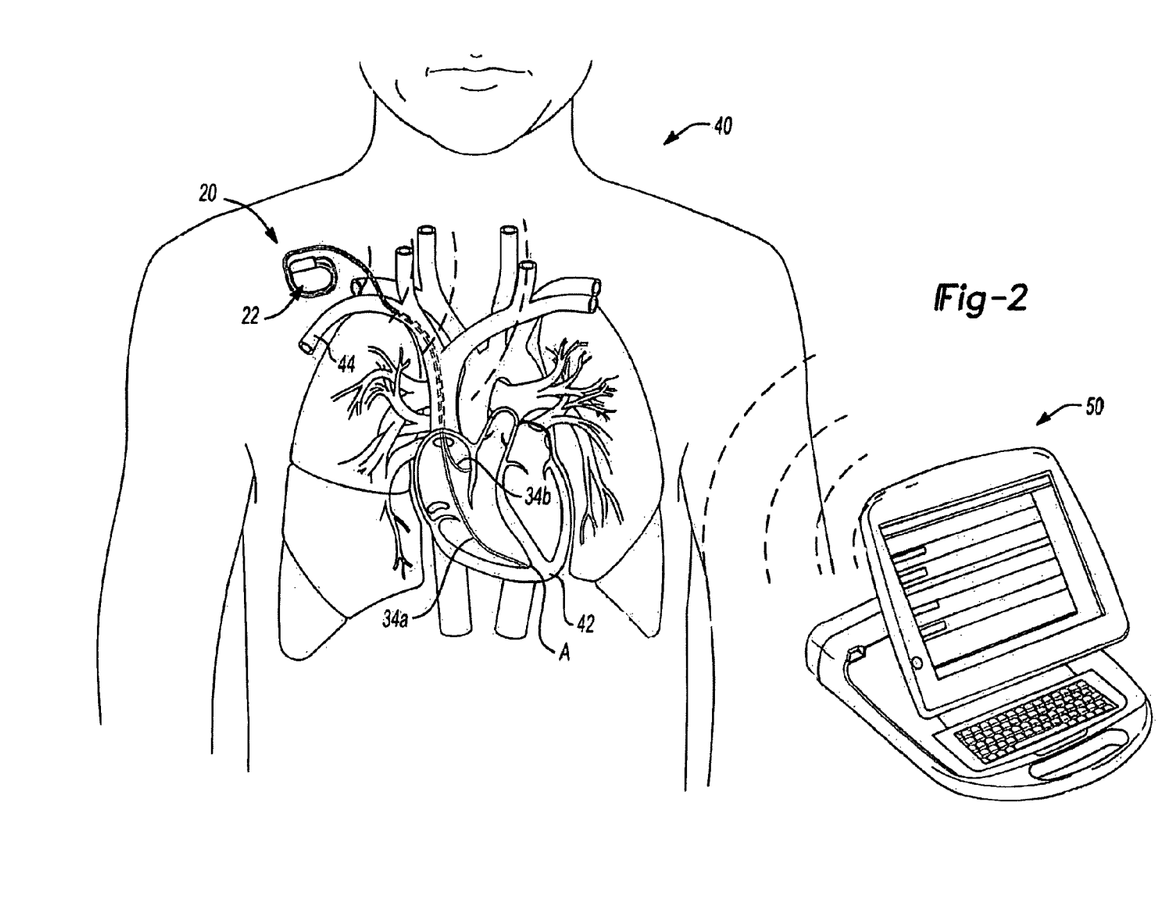
FIG. 2 is a simplified environmental view of an IMD implanted in a patient.

Contained within or associated with the case 22 can be a power device 25 (i.e., battery), a controller assembly 26, and a connector body 27. The controller assembly 26 can include a circuit board having a processor, memory, transmitter, receiver, and other appropriation portions, further discussed herein. The connector body 27 can extend from or be integrated with the case 22. The connector body 27 can include multiple ports 28 that each interconnect with a connector terminal 30 of a lead assembly 32. FIG. 1 illustrates two lead assemblies 32*a*, 32*b* where each lead assembly 32*a*, 32*b* includes lead bodies 34*a*, 34*b* extending from tip electrodes 36*a*, 36*b*. Although the IMD 20 is illustrated in FIGS. 1 and 2 as including two lead assemblies 32*a*, 32*b*, it will be understood that any number of lead assemblies 32 could be employed with the IMD 20 depending upon the malady of the patient and the particular IMD 20 employed. Moreover, the switch assembly further discussed herein can be associated with one or all of the lead assemblies 32*a*, 32*b* for the particular IMD 20 employed.

A fixation mechanism can also be included with each lead assembly 32*a*, 32*b* to affix each tip electrode 36*a*, 36*b* relative to or in a selected tissue of the patient. The fixation mechanism can be near each tip electrode 36*a*, 36*b* or define a portion of the tip electrode 36*a*, 36*b*. Fixation mechanisms can be any appropriate type, including a grapple mechanism, a helical mechanism, a drug-coated connection mechanism, and other appropriate connection mechanisms.

A majority of each lead body 34*a*, 34*b* can also be formed in a generally known and selected manner. For example, the various conductors and electrical components can be encased in silicone, polyurethane, and other appropriate materials. For example, at least one inner conductor 136 (FIG. 5) can extend from each connector terminal 30 to engage each tip electrode 36*a*, 36*b* (identified as 132*d* in FIG. 4). It will be understood by one skilled in the art, the inner conductor 136 can be one piece or multiple components that are interconnected. Also, more than one conductor can be provided, such as one conductor for each electrode in each lead assembly 32*a*, 32*b*. The inner conductor 136 can also be cannulated or include a solid or non-cannulated cable. The casing material of each lead body 34*a*, 34*b* can electrically insulate the inner electrical conductor from an external environment.

The IMD 20, including the components discussed above, can be implanted in a patient 40 as illustrated in FIG. 2. The IMD 20 can include one or more lead assemblies 32, such as the first lead assembly 32*a* and the second lead assembly 32*b*. The first lead assembly 32*a* and the second lead assembly 32*b* can be connected to the connector body 27. As one skilled in the art will understand, the position of lead bodies 34*a*, 34*b* can depend upon the type of IMD and the malady of the patient 40. For example, the lead assemblies 32*a*, 32*b* can be positioned transvenously to positions within a heart 42 or on the outside of the heart 42. The IMD 20 can be provided to pace the heart 42, defibrillate the heart 42, sense conditions of the heart 42, etc.

The IMD 20, including the case 22 and the lead bodies 34a, 34b, can be implanted using known procedures. For example, an incision can be made in a chest wall or an abdomen wall of the patient 40 and the lead assemblies 32a, 32b can be passed through selected veins to selected portions of the heart 42 of the patient 40. The case 22 can also be positioned through the incision into a chest wall or abdominal wall of the patient 40. In a selected procedure, the leads assemblies 32a, 32b can be passed through a superior vena cava 44 of the patient 40. The lead tips or tip electrodes 36a, 36b can be positioned at various positions in the heart 42, such as at the ventricles or atriums thereof. The position of the lead assemblies 32a, 32b and tip electrodes 36a, 36b can be selected for pacing, defibrillation, sensing, or other appropriate procedures. The specific implantation procedure, position of the tip electrodes 36a, 36b, and the like can depend upon the patient 40, the surgeon performing the procedure, the specifics of the lead assemblies 32a, 32b, or other considerations.

As discussed above, the IMD 20, including the case 22 and the lead assemblies 32a, 32b can include various features or controls to defibrillate or pace the heart 42. The controls can include a processor associated with the controller assembly 26 located within the case 22. The processor can be programmed to control driving a current through the lead bodies 34a, 34b to the tip electrodes 36a, 36b to defibrillate or pace the heart 42.

With continued reference to FIG. 2, a programmer or programming system 50 can be provided. The programmer 50 can include a telemetry system that is operable to wirelessly transmit a signal to the processor within the case 22. It will be understood that a wired communication system can also be used. In addition, an induction system can be used where a coil is positioned near the case 22 and a signal is sent from the programmer 50 via induction. The programmer 50 can also receive information from the IMD 20 (e.g. tachycardia rhythms, times and programming settings) to assist in providing an appropriate program for therapy and to determine if the IMD 20 is operating properly. The programmer 50 can include any appropriate programming system, including one generally known to those skilled in the art, such as the Medtronic CARELINK™ programmer, sold by Medtronic, Inc. of Minneapolis, Minn.

Moreover, the IMD 20, including the case 22 and the lead assemblies 32a, 32b, can be formed to counteract or interact with various environmental factors. For example, the lead assemblies 32a, 32b can include features or portions to re-direct or dissipate thermal energy created by an induced current. Induced currents can be created due to an external field, such as an electromagnetic field acting on the conductors of the lead assemblies 32a, 32b.

For example, according to various embodiments, the patient 40 which has the implanted IMD 20 may receive a certain therapy or diagnostic technique, such as a magnetic resonance image (MRI) scan. Although not illustrated, a MRI, generally understood by one skilled in the art, uses high frequency electromagnetic pulses and strong magnetic fields to create image data regarding the patient 40. Generally, a MRI will have a frequency of about 42 MHz per tesla. Many common MRI systems use about 1.5 tesla magnetic fields and have a corresponding RF frequency of about 63 MHz. Without being bound by the theory, the strong magnetic fields in a MRI can induce aligned spins of sub-atomic particles and the high frequency RF pulses can be used to change the alignment or otherwise affect the sub-atomic particles within the patient 40.

The strong magnetic fields and electromagnetic pulses may induce currents within the lead assemblies 32a, 32b of the IMD 20. The current induced in the lead assemblies 32a, 32b may cause certain affects, including heating, of the various lead components. According to various embodiments, such as those discussed herein, components, controls and/or mechanisms can be provided to reduce or eliminate the amount of current or thermal energy induced within each tip electrode 36a, 36b, or increase an area over which the current or thermal energy can be dissipated.

Figure 3:
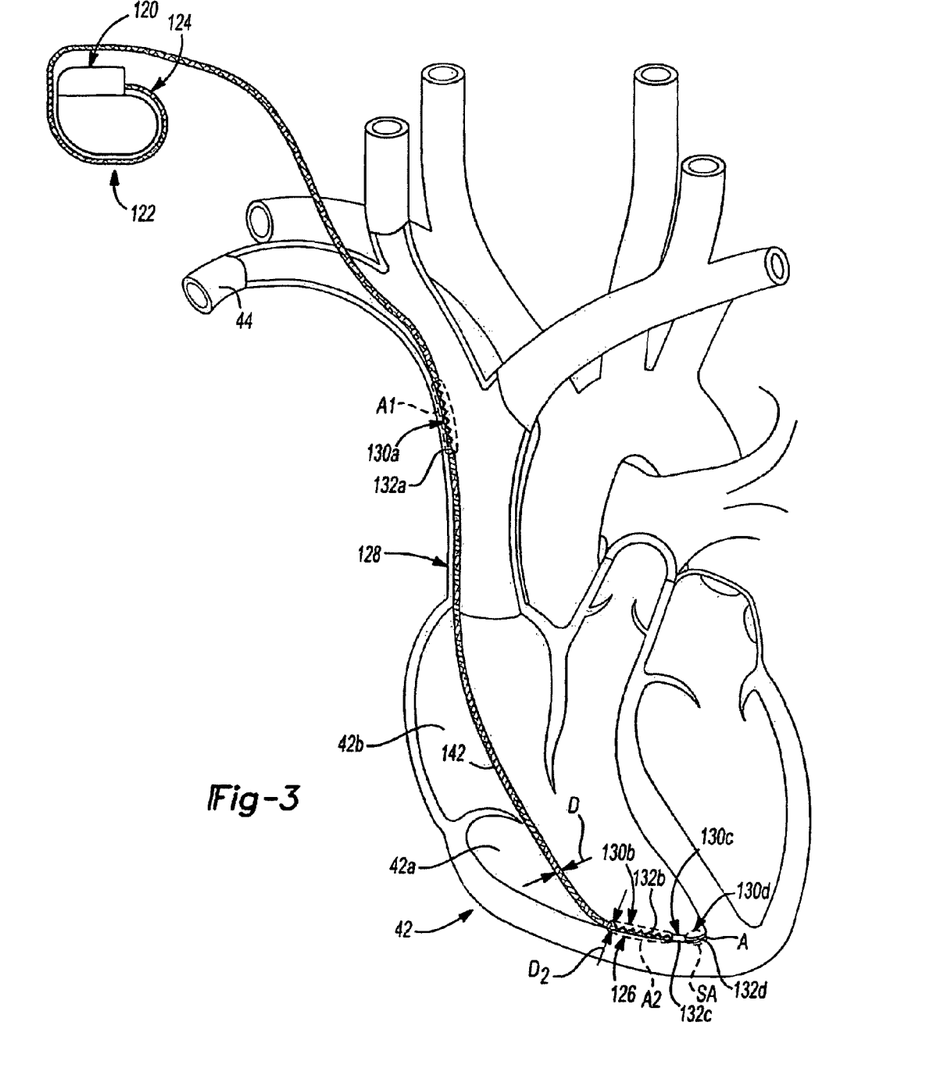
FIG. 3 is an environmental view of an ICD implanted in a patient that includes an exemplary shielded cardiac lead system.

According to various embodiments, with reference to FIG. 3, the IMD 20 can comprise an implantable cardiac device, such as an implantable cardioverter-defibrillator (ICD) 120. As the ICD 120 that will be described herein with reference to FIGS. 3-6 can be similar to the IMD 20 described with reference to FIGS. 1-2, similar reference numerals will be used to denote like components. With continued reference to FIG. 3, the ICD 120 can be used to detect and treat cardiac arrhythmias, and thus, can deliver a therapy to a desired location within the heart 42. In this regard, the ICD 120 can provide anti-tachycardia pacing, cardioversion, defibrillation, and/or bradycardia pacing, while also monitoring the heart rhythm to determine if a therapy is needed. As the ICD 120 can comprise any suitable ICD, such as the ENTRUST™ family of ICDs available from Medtronic, Inc. of Minneapolis, Minn., the ICD 120 will not be discussed in great detail herein. Briefly, however, the ICD 120 can include at least one ICD lead 122, which can be implanted into an anatomical structure, such as the heart 42. The ICD 120 can comprise a single chamber ICD that includes one lead 122 (as illustrated), a dual chamber ICD that includes two leads or a biventricular ICD that includes three leads. The lead 122 can both sense the electrical activity of the heart 42 and can also deliver electrical energy to pace the heart 42. The lead 122 can include a proximal end 124, a distal end 126, a body 128 and at least one electrode assembly 130.

As will be discussed further herein, each electrode assembly 130 can include an electrode 132 and a transmission member 134, which includes an inner conductor 136 and an insulative member 138. Briefly, the electrode 132 can be in contact with the anatomical structure to deliver a therapy to the anatomical structure, such as an electrical pulse, and can be in communication with the inner conductor 136 to receive the therapy. Thus, the inner conductor 136 can be in electrical communication with the electrode 132 and the ICD 120 to receive the therapy. In this example, the lead 122 can include four electrode assemblies 130, labeled 130a, 130b, 130c, 130d from the proximal end 124 to the distal end 126 of the lead 122. It should be noted that while the lead 122 is illustrated with four electrode assemblies 130 in FIG. 3, the lead 122 may have any number of electrode assemblies 130.

The proximal end 124 of the lead 122 can include a connector portion 140. As the connector portion 140 can be generally known, the connector portion will not be discussed in great detail herein. Briefly, however, the connector portion 140 can electrically couple the lead 122 to the ICD 120. The distal end 126 can terminate within the anatomical structure adjacent to the desired location for the delivery of the therapy, and generally, for example, can terminate adjacent to an apex of the heart 42, such as the right ventricular apex A, a ventricle, such as the right ventricle 42a, or other chambers, such as the right atria 42b, of the heart 42. As will be discussed, one electrode 132 of the at least one electrode assembly 130 can be coupled to the distal end 126 to deliver a therapy to the atrium A of the heart 42.

The body 128 of the lead 122 can extend from the proximal end 124 to the distal end 126. With reference FIG. 5, the body 128 can include an overlay 142, at least one conductive member or shield 144, and a multilumen member 146. The body 128 can serve to protect, carry and guide the at least one electrode assembly 130 through the anatomical structure. The overlay 142 can comprise any suitable biocompatible material, such as a biocompatible polymer, and can generally be composed of polyurethane. The overlay 142 can be disposed over and coupled to the at least one conductive member 144. For example, the overlay 142 can be formed onto the at least one conductive member 144 such that the overlay 142 is molded onto and penetrates through the at least one conductive member 144 thereby encapsulating the at least one conductive member 144 within the overlay 142 (illustrated in phantom in FIG. 5).

Figure 5:
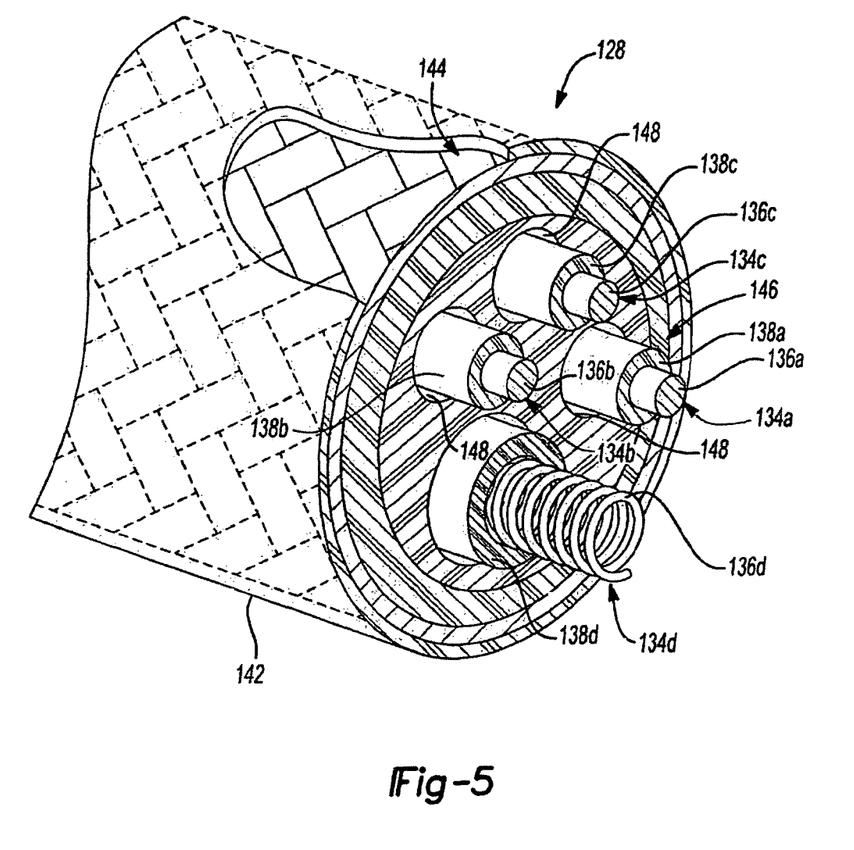
FIG. 5 is a perspective cut away view of the cardiac lead system of FIG. 4 taken along line 5-5 of FIG. 4.

The at least one conductive member 144 can comprise a first conductive braid 144a and a second conductive braid 144b. The at least one conductive member 144 can generally extend for a majority of a length of the lead 122, and can generally be electrically coupled to the electrode 132 positioned near a proximal end 124 of the lead 122. It will be understood that although the at least one conductive member 144 is illustrated and described herein as comprising a braid, the at least one conductive member 144 could also comprise any desired shape or structure, such as a coil, continuous tubular structure, etc., and thus, need not be composed of a plurality of interwoven conductive members as shown. The first conductive braid 144a can extend from the proximal end 124 of the lead 122 to the electrode assembly 130 located near a proximal end of the electrode assembly 130a. The second conductive braid 144b can extend from a distal end of the electrode assembly 130a to a proximal end of a second electrode assembly 130b. The first conductive braid 144a and the second conductive braid 144b can each be in electrical communication with the electrode 132a of the first electrode assembly 130a to dissipate a current induced in the first conductive braid 144a and the second conductive braid 144b through the electrode 132a.

Figure 6:
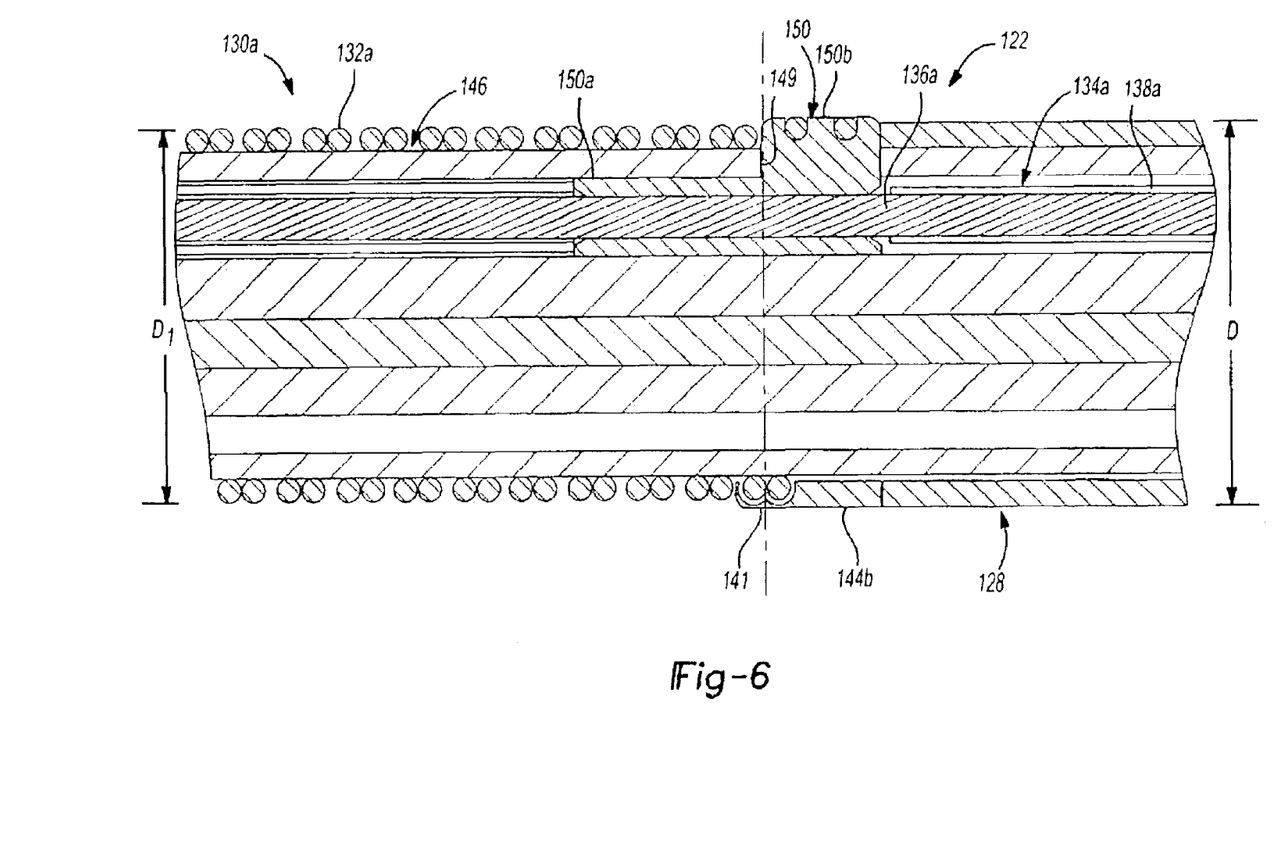
FIG. 6 is a cross-sectional view of the cardiac lead system of FIG. 4 taken along line 6-6 of FIG. 4.

The multilumen member 146 can be disposed within the first conductive braid 144a and the second conductive braid 144b. The multilumen member 146 can define at least one channel 148 for receipt of each of the inner conductors 136 associated with the electrode assemblies 130. Generally, the multilumen member 146 can be composed of a biocompatible material, such as a biocompatible polymer, for example, a silicone rubber. The at least one channel 148 can receive each of the inner conductors 136 of the electrode assemblies 130, and can serve as a conduit that guides each of the inner conductors 136 from the ICD 120 to the electrode 132 of the respective electrode assembly 130. With reference to FIG. 6, the multilumen member 146 can also include one or more apertures 149 that extend out of a sidewall of the multilumen member 146. The apertures 149 can enable the various electrode assemblies 130 to be electrically coupled to the inner conductors 136 passing through the multilumen member 146.

With reference to FIGS. 3-6, selected ones of the electrode assemblies 130 can be operable to deliver the therapy to the anatomical structure, and a selected one of the electrode assemblies 130 can be operable to sense electrical activity at a desired site in the anatomical structure. The electrode assemblies 130 can include a first electrode or first defibrillator electrode assembly 130a, a second electrode or second defibrillator electrode assembly 130b, a sense electrode or ring electrode assembly 130c and a tip electrode assembly 130d.

Figure 4:
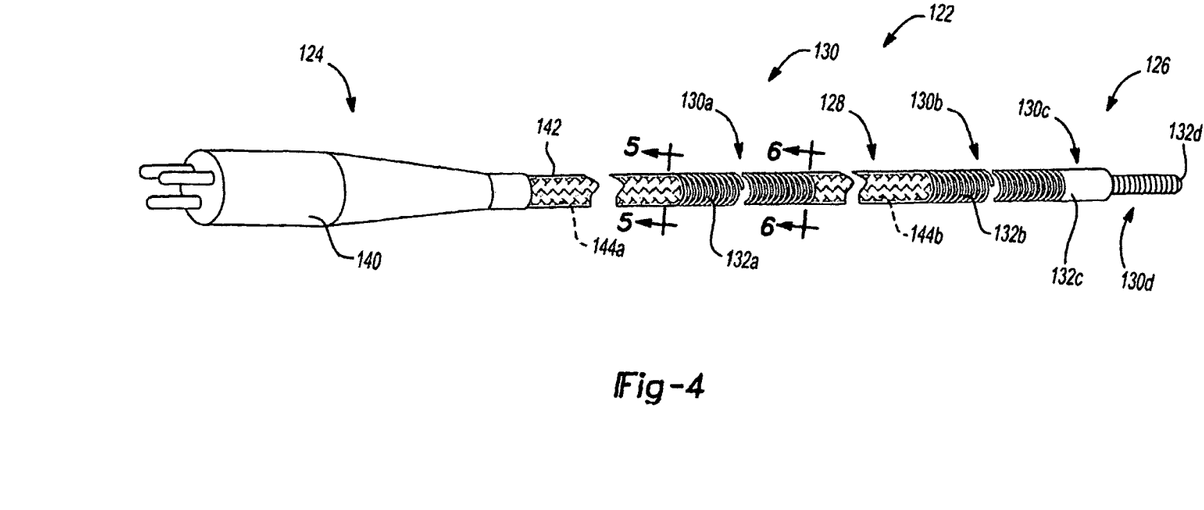
FIG. 4 is a perspective view of the exemplary shielded cardiac lead system according to various embodiments.

With reference to FIGS. 4-6, the first defibrillator electrode assembly 130a can be coupled to the body 128 such that the first defibrillator electrode assembly 130a can be disposed between the proximal end 124 and the distal end 126. The first defibrillator electrode assembly 130a can include the first defibrillator electrode 132a and transmission member 134a. Generally, the first defibrillator electrode assembly 130a can be coupled to the body 128 such that when the lead 122 is implanted within the anatomical structure, such as the heart 42, the first defibrillator electrode 132a can be adjacent to a first portion of the anatomical structure, such as the superior vena cava 44 (FIG. 3).

With reference to FIGS. 3 and 6, the first defibrillator electrode 132a can have a first diameter D1 and a first surface area (generally indicated as A1 in phantom). The first diameter D1 can be substantially equivalent to a diameter D of the overlay 142 so that when the first defibrillator electrode 132a is coupled to the body 128, a smooth transition exists between the first defibrillator electrode 132a and the body 128. The first surface area A1 can be larger than a surface area of the electrode 132d of the distalmost electrode assembly 130d, generally indicated as SA in phantom. Generally, the first surface area A1 can range from about 400 square millimeters to about 1000 square millimeters, and generally can range from about 750 square millimeters to about 850 square millimeters. As shown in FIG. 6, the first defibrillator electrode 132a can be coupled to the at least one conductive member 144, the multilumen member 146 of the body 128, and the transmission member 134a. The transmission member 134a can pass through one of the channels 148 of the multilumen member 146, and can be in communication with and responsive to the ICD 120 to transmit an electrical signal or charge to the first defibrillator electrode 132a. The transmission member 134a can include the inner conductor 136a that is encased by or coated with an insulative member 138a, such as a biocompatible polymer, for example, a fluoropolymer.

With reference to FIGS. 4 and 6, the first defibrillator electrode 132a can be coupled to and in communication with the first conductive braid 144a and the second conductive braid 144b (FIG. 6). Generally, the location of the first defibrillator electrode assembly 130a can be fixed relative to a length of the lead 122 between the proximal end 124 and the distal end 126. The first defibrillator electrode 132a can be coupled to the first conductive braid 144a and the second conductive braid 144b, via any suitable mechanism that enables electrical communication between the first defibrillator electrode 132a, the first conductive braid 144a and the second conductive braid 144b. These mechanisms can include welding, crimping, conductive adhesives, conductive fasteners, etc., as generally indicated by reference numeral 141 in FIG. 6.

Accordingly, if a current is induced in the first conductive braid 144a and/or second conductive braid 144b from an external electric field, such as that generated by an MRI, the current and heat generated by the induced current can flow from the first conductive braid 144a and/or second conductive braid 144b into the first defibrillator electrode 132a, which is grounded by the body. With reference to FIG. 3, as the first defibrillator electrode 132a is adjacent to the anatomical structure, such as the superior vena cava 44, and has a large surface area A1, the current can be dissipated by the first defibrillator electrode 132a into the anatomical structure. This can ensure that if a current is induced in the first conductive braid 144a and/or second conductive braid 144b, any induced current flows to the electrode assembly 130 that has the largest surface area, such as the first defibrillator electrode assembly 130a. In other words, the at least one outer conductive member or shield 144 shields and prevents currents from being induced in the inner conductors 136 which are surrounded by the at least one outer conductive member or shield 144, thereby preventing induced currents from flowing to a smaller surface electrode assembly 130, such as the tip electrode 132d.

With reference to FIG. 6, the first defibrillator electrode 132a can be coupled to the transmission member 134a disposed in the multilumen member 146 via a connection 150. The connection 150 can couple the first defibrillator electrode 132a to the inner conductor 136a to enable electrical communication between the inner conductor 136a and the first defibrillator electrode 132a. The connection 150 can include a first end 150a and a second end 150b. The first end 150a can be crimped to the inner conductor 136a of the transmission member 134a, while the second end 150b can be coupled to the first defibrillator electrode 132a, through welding, for example.

With reference to FIGS. 3 and 4, the second defibrillator electrode assembly 130b can be coupled to the body 128 such that the second defibrillator electrode assembly 130b can be disposed near the distal end 126 of the lead 122, between the first electrode assembly 130a and the ring electrode assembly 130c. Generally, the location of the second defibrillator electrode assembly 130b can be fixed relative to the length of the lead 122 between the proximal end 124 and the distal end 126. The second defibrillator electrode assembly 130b can include the second defibrillator electrode 132b and the transmission member 134b. Generally, the second defibrillator electrode assembly 130a can be coupled to the body 128 such that when the lead 122 is implanted within the anatomical structure, such as the heart 42, the second defibrillator electrode 132b can be adjacent to a second portion of the anatomical structure, such as a right ventricle 42a of the heart 42 (FIG. 3).

With reference to FIG. 3, the second defibrillator electrode 132b can have a second diameter D2 and a second surface area (generally indicated as A2 in phantom). The second diameter D2 can be substantially equivalent to the diameter D of the overlay 142 so that when the second defibrillator electrode 132b is coupled to the body 128, a smooth transition exists between the second defibrillator electrode 132b and the body 128. The second surface area A2 can be larger than the surface area SA of the tip electrode assembly 130d, but can be smaller than the first surface area A1 of the first defibrillator electrode 132a. Generally, the second surface area A2 can range from about 300 square millimeters to about 800 square millimeters, and generally can range from about 500 square millimeters to about 650 square millimeters.

The second defibrillator electrode 132b can be adjacent to, but not in electrical communication with the at least one conductive member 144, and can be coupled to the multilumen member 146 of the body 128, and the transmission member 134b. As the second defibrillator electrode 132b can be adjacent to, but not in electrical communication with the second conductive braid 144b, this can ensure that if a current is induced in the second conductive braid 144b, the current is communicated to the first defibrillator electrode 132a, which has a larger surface area A1 to dissipate the current, and can dissipate the current in a generally non-critical area of the anatomical structure. The transmission member 134b can pass through one of the channels 148 of the multilumen member 146, and the inner conductor 136b can be in communication with and responsive to the ICD 120 to transmit an electrical signal or charge to the second defibrillator electrode 132b. The inner conductor 136b can be encased by or coated with the insulative member 138b, which can comprise a biocompatible polymer, for example a fluoropolymer.

The second defibrillator electrode 132b can be coupled to the inner conductor 136b disposed in the multilumen member 146 via a suitable connection, such as the connection 150 (not specifically shown). In this regard, if employed, the connection 150 can electrically couple the second defibrillator electrode 132b to the inner conductor 136b. As the connection 150 between the inner conductor 136b and the second defibrillator electrode 132b can be substantially similar to that discussed with regard to the first defibrillator electrode assembly 130a, the connection 150 will not be discussed with regard to the second defibrillator electrode assembly 130b.

With reference to FIGS. 3 and 4, the sense electrode or ring electrode assembly 130c can be coupled to the body 128 such that the ring electrode assembly 130c can be disposed near the distal end 126, between the second electrode assembly 130b and the tip electrode assembly 130d. As the ring electrode assembly 130c can be generally known in the art, and can be similar to the ring electrode assembly of the SPRINT QUATTRO SECURE™ cardiac lead commercially available from Medtronic, Inc. of Minneapolis, Minn., the ring electrode assembly 130c will not be discussed in great detail herein. Briefly, however, the ring electrode assembly 130c can include airing electrode 132c (FIG. 4) and a transmission member 134c (FIG. 5). The ring electrode 132c can be adjacent to the anatomical structure, such as the heart 42, to receive electrical signals indicative of the electrical activity of the heart 42. These electrical signals can be transmitted to the ICD 120 via the inner conductor 136c of the transmission member 134c. The transmission member 134c can be disposed in one of the channels 148 of the multilumen member 146.

With reference to FIGS. 3-5, the tip electrode assembly 130d can extend beyond the multilumen member 146, and can contact the anatomical structure at a distalmost part, such as the right ventricular apex A of the heart 42. As the tip electrode assembly 130d can be generally known in the art, and can be similar to the tip electrode of the SPRINT QUATTRO SECURE™ cardiac lead commercially available from Medtronic, Inc. of Minneapolis, Minn., the tip electrode assembly 130d will not be discussed in great detail herein. Briefly, however, the tip electrode assembly 130d can include a tip electrode 130d and the transmission member 134d. The inner conductor 136d can electrically couple the tip electrode 132d to the ICD 120 so that the tip electrode 132d can to receive electrical signals and deliver a therapy, such as a pacing therapy, to the distalmost part of the anatomical structure. As illustrated in FIG. 3, the surface area SA of the tip electrode 132d can be smaller than the first surface area A1 of the first defibrillator electrode 132a and the second surface area A2 of the second defibrillator electrode 132b, and can range from about 1 square millimeter ($mm^2$) to about 8 square millimeters ($mm^2$).

With reference to FIGS. 3-6, in order to assemble the lead 122, in ah exemplary process, the transmission members 134 can be inserted into the multilumen member 146. Then, the connection 150 can be coupled to the respective inner conductors 136 to couple the inner conductors 136 to the respective electrodes 132 (FIG. 6). The first conductive braid 144a and the second conductive braid 144b can then be positioned over the multilumen member 146. Next, the overlay 142 can be formed on, applied or extruded onto the first conductive braid 144a and second conductive braid 144b. The first conductive braid 144a and second conductive braid 144b can then be coupled to the first defibrillator electrode 132a such that the first conductive braid 144a and second conductive braid 144b are in communication with the first defibrillator electrode 132a. In one embodiment, the outer conductive member 144 can be combined with the overlay 142 in a separate operation, such as a continuous extrusion process or a discrete assembly and heating reflow operation.

With the lead 122 assembled, the lead 122 can be coupled to the ICD 120, and the lead 122 and ICD 120 can be implanted into the anatomical structure. Generally, the lead 122 can be implanted such that the first defibrillator electrode 132a is adjacent to the superior vena cava 44, the second defibrillator electrode 132b is within the right ventricle 42a, and the tip electrode 132d is adjacent to the right ventricular apex A of the heart 42 (FIG. 3). If the anatomical structure encounters an external field, such as that generated by an MRI, a current may be induced in the at least one outer conductive member 144, which can serve to protect or shield the inner conductors 136 from the induced current, and thereby prevent the transmission of the induced current to an electrode assembly with a small surface area, such as the tip electrode 132d.

In this regard, as the at least one outer conductive member 144 covers, surrounds or shields the inner conductors 136 of the electrode assemblies 130, the external field generated by the MRI can induce a current in the at least one outer conductive member 144, thereby protecting or shielding the inner conductors 136 from the effects of the external field. Further, as the at least one outer conductive member 144 is in communication with the first defibrillator electrode 132a, the current and heat induced in the at least one outer conductive member 144 can be dissipated by the first defibrillator electrode 132a into the anatomical structure, which can serve to as a ground for the at least one outer conductive member 144.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. An implantable medical device operable to provide a therapy to an anatomical structure comprising:
   a therapy device configured to be implanted in a portion of the anatomical structure and operable to generate the therapy for the anatomical structure;
   a lead having a proximal end, a distal end and a lead body that includes a first outer conductive braid, a second outer conductive braid and a multilumen member, the first outer conductive braid and the second outer conductive braid disposed about the multilumen member;
   a first electrode fixedly coupled between the proximal end and the distal end of the lead such that the first electrode being configured to be positioned adjacent to a first portion of the anatomical structure, the first electrode in communication with the first outer conductive braid and the second outer conductive braid;
   a first inner conductor passing through a portion of the multilumen member and in electrical communication with the first electrode and configured to deliver a therapy to the first portion of the anatomical structure;
   a tip electrode extending beyond the distal end of the lead;
   a tip inner conductor passing through a portion of the multilumen member and in electrical communication with the tip electrode and configured to deliver a therapy to a second portion of the anatomical structure;
   a second electrode coupled adjacent to the tip electrode at the distal end of the lead such that the second electrode being configured to be positioned adjacent to a third portion of the anatomical structure;
   a second inner conductor passing through a portion of the multilumen member and in electrical communication with the second electrode and configured to deliver a therapy to the third portion of the anatomical structure; and
   wherein the first outer conductive braid being disposed between the proximal end of the lead and the first electrode, the second outer conductive braid being disposed between the first electrode and the second electrode, and the first electrode configured to dissipate a current induced in the first outer conductive braid and second outer conductive braid, via the first portion of the anatomical structure.

2. The device of claim 1, wherein the therapy device being an implantable cardioverter-defibrillator (ICD).

3. The device of claim 2, further comprising:
   a ring electrode coupled adjacent to the tip electrode at the distal end of the lead such that the ring electrode being configured to be positioned adjacent to a fourth portion of the anatomical structure, the ring electrode in communication with a ring inner conductor and configured to transmit a signal indicative of electrical activity at the fourth portion of the anatomical structure.

4. The device of claim 1, wherein the first outer conductive braid and the second outer conductive braid shields the at least one inner conductor from an external field.

5. The device of claim 1, wherein the first outer conductive braid and the second outer conductive braid are coated with a biocompatible polymer.

6. The device of claim 5, wherein the first electrode comprises a first defibrillator electrode, and the second electrode comprises a second defibrillator electrode.

7. The device of claim 6, wherein the first defibrillator electrode and the second defibrillator electrode are electrically coupled to the first inner conductor and the second inner conductor, respectively, in such a manner that the lead has a substantially uniform diameter.

8. The device of claim 1, wherein the first electrode has a first surface area, the second electrode has a second surface area, and the tip electrode has a third surface area, and the first surface area being greater than the second surface area and the third surface area.

* * * * *